United States Patent [19]

Wallace

[11] 4,247,393

[45] Jan. 27, 1981

[54] HEMODIALYSIS ASSIST DEVICE

[76] Inventor: Richard A. Wallace, 7304 SW. 53 Ave., Portland, Oreg. 97219

[21] Appl. No.: 2,759

[22] Filed: Jan. 11, 1979

Related U.S. Application Data

[63] Continuation-in-part of Ser. No. 875,223, Feb. 10, 1978, abandoned, and a continuation-in-part of Ser. No. 779,985, Mar. 3, 1977, abandoned, and a continuation-in-part of Ser. No. 558,171, Mar. 13, 1975, abandoned.

[51] Int. Cl.³ .................... B01D 31/00; B01D 13/00
[52] U.S. Cl. .................................. 210/638; 210/502; 210/927; 210/321.2; 210/646
[58] Field of Search ............... 210/22 A, 40, 22 C, 210/DIG. 23, 22 D, 41, 321 B, 321 A, 505, 502; 128/214 R

[56] References Cited

U.S. PATENT DOCUMENTS

| | | | |
|---|---|---|---|
| 3,388,803 | 6/1968 | Scott | 210/321 B |
| 3,573,158 | 3/1971 | Pall et al. | 210/505 X |
| 3,608,729 | 9/1971 | Haselden | 210/321 A |
| 3,703,959 | 11/1972 | Raymond | 210/321 B |
| 3,742,946 | 7/1973 | Grossman | 128/214 R |
| 3,775,344 | 11/1973 | Amagi et al. | 210/40 X |
| 4,036,747 | 7/1977 | Hori et al. | 210/22 A |

OTHER PUBLICATIONS

Grossman, "Dessicant-Induced Ultrafiltration Across an Artificial Membrane," from *J. of Applied Phys.*, 2/1972, pp. 283 and 284.

*Primary Examiner*—Frank A. Spear, Jr.
*Attorney, Agent, or Firm*—Flehr, Hohbach, Test, Albritton & Herbert

[57] ABSTRACT

A hemodialysis assist device including a normally non-flowing aqueous sorbents slurry medium chamber and at least one blood flowthrough passage separated therefrom by a semipermeable membrane of the flat plate, pleated flat plate, hollow fiber or hemicapillary type. The sorbents medium is in the form of a thixotropic network slurry of fine charcoal powder, fine phosphate ion-binding particles, or both. The sorbent particles are substantially retained in place even during ultrafiltration of excess body fluids across the membrane. This retention is assisted by the addition of a small quantity of fine cellulose-based polymer binder capable of forming an interlocking thixotropic network with the sorbents. The assist device may be used in conjunction with a conventional hemodialyzer to reduce dialysis treatment time, as well as to effectively remove urea. In addition, this blood detoxification device can be used also to treat the problems of hyperphosphatemia and hyperlipidemia.

13 Claims, 6 Drawing Figures

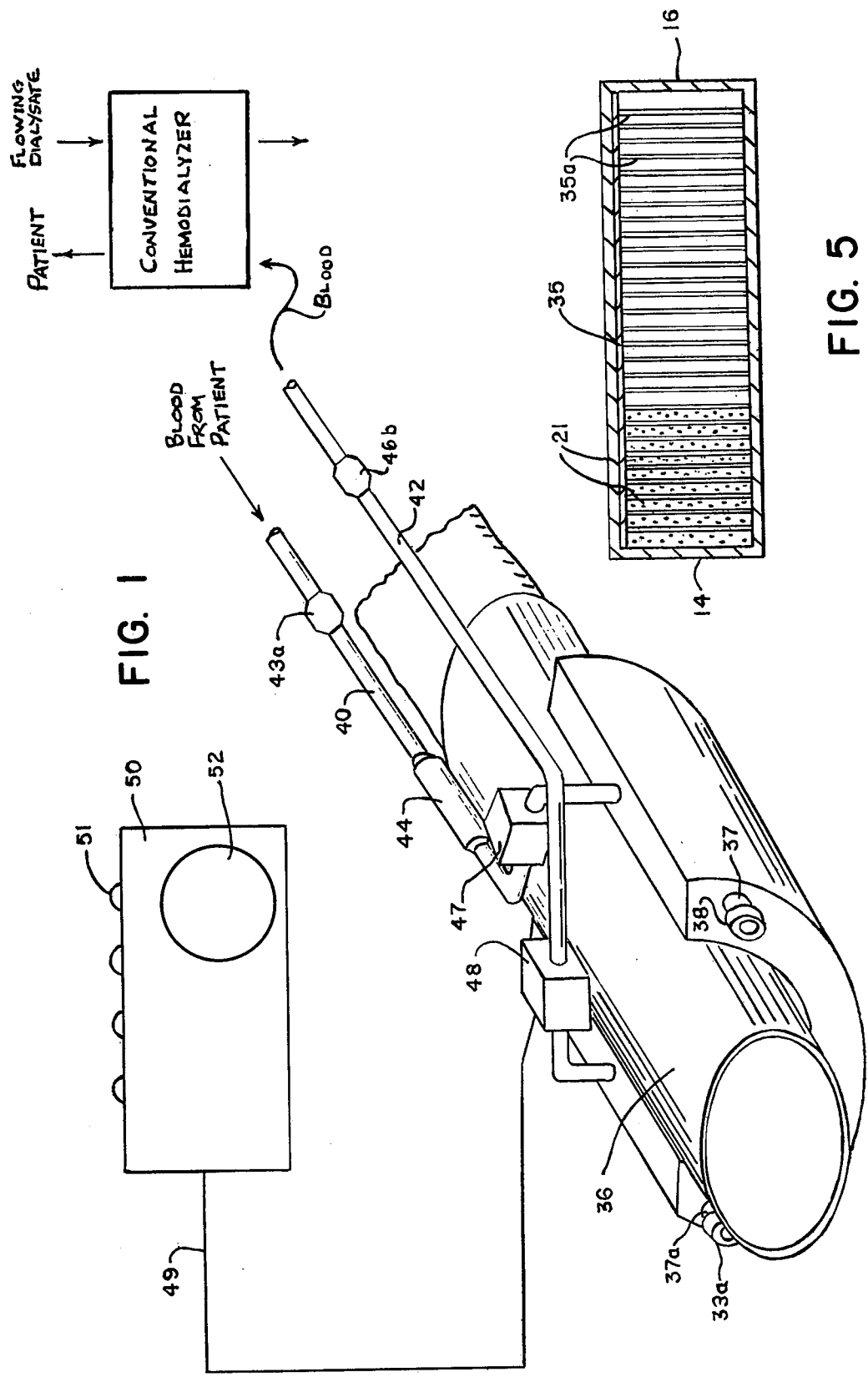

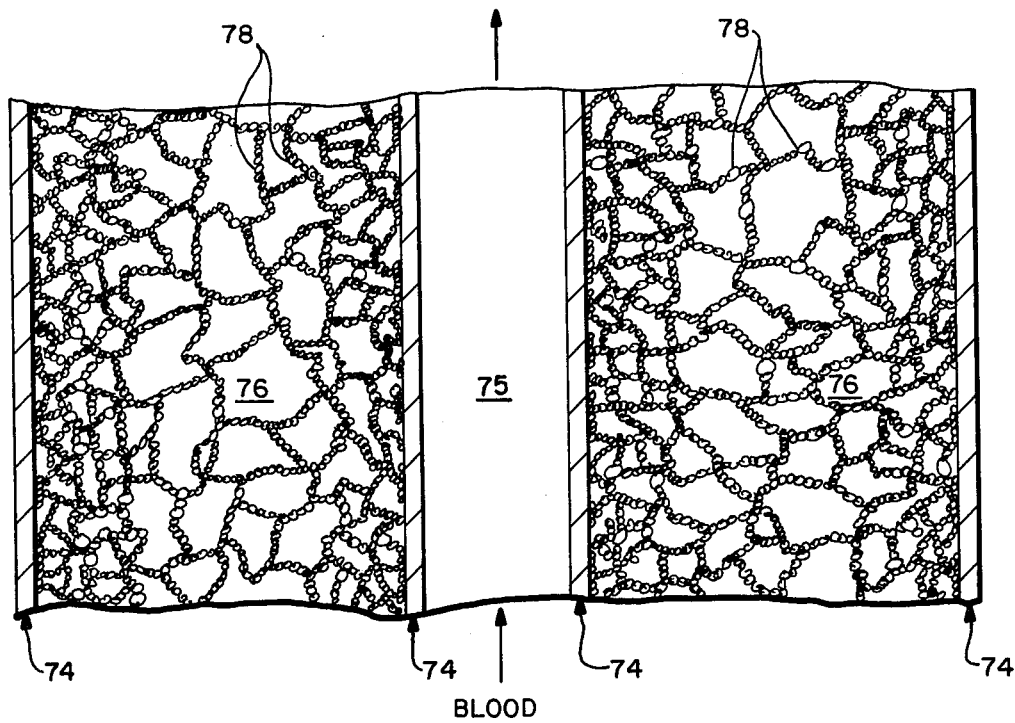
FIG.—6

HEMODIALYSIS ASSIST DEVICE

CROSS-REFERENCE TO RELATED APPLICATIONS

This application is a continuation-in-part of my copending application, Ser. No. 875,223, filed Feb. 10, 1978 of the same title, now abandoned, and its parent application, Ser. No. 779,985, filed Mar. 3, 1977, also of the same title, now abandoned, and its parent application, Ser. No. 558,171, filed Mar. 13, 1975 entitled "Wearable Artificial Kidney", now abandoned.

BACKGROUND OF THE INVENTION

The present invention relates to a hemodialysis assist device which may be used in conjunction with a conventional flowing dialyzate fluid hemodialysis device.

The conventional method of treating a person suffering from kidney disease or kidney failure is by use of an artificial kidney machine. Blood is withdrawn from one blood vessel, usually an artery, and subsequently returned into another blood vessel, usually a vein, after passage through a dialyzer which includes a number of separate flow passages for blood and dialysis fluid on opposite sides of a dialysis membrane. However, there is an inadequate number of available artificial kidney machines and trained personnel to operate them. Use of such machines usually requires immobilization of the patient for up to thirty hours per week in the hospital with an average of six to eight hours for each treatment. High level retention of phosphate continuously builds up in the serum of the patient (hyperphosphatemia) because the phosphate ion transfer across the membrane in such hemodialysis treatments is slow. Severe crippling can result from longterm elevations in serum phosphate.

One suggested alternative to a conventional hemodialyzer is set forth in U.S. Pat. No. 3,608,729 (Haselden). There, dialysate fluid is disclosed as being contained in a stationary form on the opposite side of a semi-permeable membrane from the blood. Dialysis fluid-saturated absorbent material is disclosed as being deposited as a compact layer in finely divided form as a filter cake or as a layer of paste away from the flowing blood. The disclosed adsorbent materials include charcoal or an ion-exchange resin. The patent suggests that urease enzyme could be employed to break down urea to form ammonia which is adsorbed by the adsorbent.

The Haselden U.S. Pat. No. 3,608,729 is, as a hemodialysis device for patients in chronic renal failure, deficient in a number of important respects. Firstly, the adsorbent material is deposited as a layer of paste. If it was held in this state, it would tend to block efficient dialysis across the membrane. On the other hand, if the particles loosened, it would tend to settle to the bottom of the apparatus by gravity with insufficient mass transfer contact with the dialyzed components of the blood. Furthermore, the removal of excess body fluids in the blood which accumulate daily could not be performed simultaneously or intermittently with dialysis. That is, application of a vacuum to the dialysis fluid chamber would tend to remove dialysis fluid together with the adsorbents and urease enzyme from the sealed dialysate cavities.

Another attempt at a wearable dialysis apparatus is disclosed in U.S. Pat. No. 3,388,803. This device is contoured to the human body and includes blood inlet and blood outlet conduits formed by semipermeable membranes. On the outside of the tubing is dialysate fluid. Uric acid is the only substance which the patent indicates as being removable from the blood in the dialysate fluid. It is incapable of removing toxic waste metabolites, such as urea, from the blood and suffers from the other deficiencies set forth with respect to U.S. Pat. No. 3,608,729.

In another approach, set forth in a paper by Charles M. Grossman, entitled "Dessicant-Induced Ultrafiltration Across An Artificial Membrane", *J. Applied Physiology*, 32; No. 2, February 1972, urea is transferred across a membrane into a desiccant compartment. A Sephadex gel is used in the compartment together with urease enzyme and an ion retention resin. The paper indicates that the ammonium ion produced by the urease enzyme is reduced by 90% by using an ion retention resin.

The stated purpose and function of Grossman's Sephadex gel and agar natural gels is to promote water adsorption by means of their desiccant nature. It is well known that Sephadex dextran gel tends to release carbohydrate chain molecules and natural degradation polysaccharide segments, at sizes below average molecular weights of 20–25,000. These molecules can readily diffuse into the patient's blood resulting in pyrogenic action and very harmful immunological responses. Agar gel comprises the collagen protein. Similarly, dangerous pyrogenic and immunological reactions result when collagen fragments and molecules enter into the patient's blood.

Grossman U.S. Pat. No. 3,742,946 relates to the same type of device as the aforementioned article. It mentions that charcoal or zirconium can be used to remove salicylates and barbituates.

None of the above devices using nonflowing dialysate fluid are effective replacements for conventional hemodialysis units. Furthermore, their authors do not suggest the importance of a nonflowing dialysate fluid hemodialysis assist unit for use in conjunction with a conventional hemodialyzer which would reduce treatment time, and treat the problems of elevated serum phosphate and lipid levels in patients. Furthermore, this would reduce cost of treatment by shortening dialysis time thereby increasing the cost-effectiveness of dialysis centers and home dialysis.

SUMMARY OF THE INVENTION AND OBJECTS

It is an object of the present invention to provide a highly efficient nonflowing sorbent hemodialysis-assist device which is capable of shortening the time of treatment by use in conjunction with a conventional flowing dialysate fluid hemodialysis.

It is a particular object of the invention to provide such an auxiliary device used in conjunction with an artificial kidney device.

It is another object of the invention to provide an auxiliary device of the foregoing type capable of assisting in reducing the level of organic uremic toxins, particularly middle molecules, also serum phosphate, lipids, and drugs.

It is a further object of the invention to provide a hemodialysis assist device of the above type capable of removing excess body fluids by transmembrane ultrafiltration without disturbing the efficiency of sorption.

Other objects and features of the invention will be apparent from the following description and appended drawings in which the preferred embodiments have been set forth in detail.

In accordance with the above objects, an auxiliary hemodialysis-assist device has been provided which may be used in conjunction with a conventional flowing dialysate fluid hemodialysis unit. It includes a nonflowing aqueous thixotropic slurry network in the flow-through passage of a hemodialyzer on the opposite side of the dialysis medium from the flowing blood in which dialysate would flow in a conventional hemodialyzer. The slurry medium includes (a) fine activated charcoal powder (average diameter less than 150 microns) which forms open aggregate chains strongly adhered to the membrane surface for highly efficient sorption of metabolic wastes and enhanced clearances of middle molecules and lipids and/or (b) phosphate ion-binding particles of similar size are dispersed to form the same type of structure. The sorbents are retained substantially in place therein even during ultrafiltration of excess body fluids. This retention is assisted by the addition of a small quantity of fine cellulose-based polymer binder capable of forming an interlocking thixotropic network with the sorbents. The device may be used in conjunction with a conventional hemodialyzer. However, the device itself does not need dialysate solution nor any associated dialysate hardware or apparatus.

BRIEF DESCRIPTION OF THE DRAWINGS

FIG. 1 is a schematic view of a hemodialysis assist device worn by a patient used in conjunction with a conventional hemodialyzer.

FIG. 5 is a cross-sectional view along line 5—5 of FIG. 2 illustrating a fiber separator.

FIG. 6 is a schematic cross-sectional view of the nonflowing side of a plate-type hemodialysis assist device illustrating the sorbent thixotropic network in magnification.

DETAILED DESCRIPTION OF THE PREFERRED EMBODIMENTS

Figure 3:
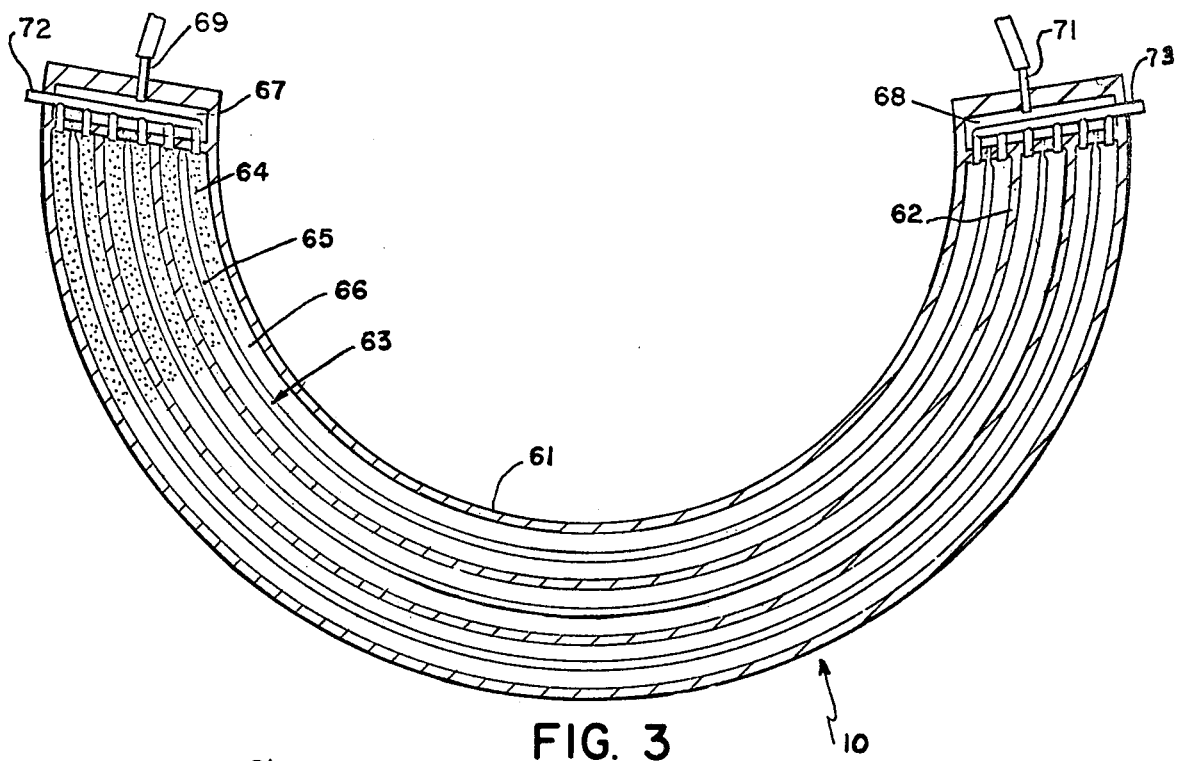
FIGS. 2 and 3 are cross-sectional schematic views of cartridges according to the present invention, of the hollow fiber and plate-type, respectively.

In general, the present invention is directed to an auxiliary hemodialysis assist device for use in conjunction with a conventional hemodialyzer. As illustrated, the present device conforms to the arm. However, since use of a large conventional hemodialyzer is required, it is more convenient to use it in series with the conventional hemodialyzer. Thus, the patient need not wear the hemodialysis assist device.

The principles of hemodialysis of blood across a semipermeable membrane used in conventional artificial kidney machines are applicable to the blood side of the membrane in the present hemodialysis assist device. That is, blood is directed from an arterial connection through the device and returns through a venous connection to the body. In the assist device, the blood is directed along a blood flowthrough passage surrounded by a conventional semipermeable dialysis membrane of a thickness on the order of 5 to 20 microns with openings of sufficient size to pass the primary toxic elements of the blood (e.g., urea, uric acid, creatinine, and so-called middle molecules, such as Vitamin $B_{12}$ and inulin, molecular weights range from about 400 to 5200) but to block the passage of high molecular weight components of the blood, e.g., greater than 20–25,000 molecular weight. It is well to point out here that ultrathin cellulosic membranes less than 10 microns thick would provide extremely high solute removal rates in the hemodialysis assist device of the present invention. Any number of conventional semipermeable membranes may be employed such as regenerated cellulose and cellulose acetate. Thus, when an excessive content of low molecular weight waste metabolites exists in the blood in comparison to the area on the opposite side of the membrane, the concentration imbalance will be corrected by passage through the membrane of such metabolites until concentration balance is again achieved.

Referring to FIG. 5, an embodiment of the assist unit is illustrated using the basic cartridge assembly of a conventional artificial kidney device of the hollow fiber type. The device 10, includes a hollow housing 11 bounded by generally flat facing end walls 12 and 13, and side walls 14 and 16. A port 15 is included in wall 16 and port 15a in wall 14.

Although any suitable material which does not contaminate the blood may be used to construct housing 11, it is preferable to form the same of a transparent or translucent polymeric material such as rigid polymethylmethacrylate or polycarbonate, or a flexible thermoplastic (e.g., polyethylene or polyvinylchloride or its copolymers) to view possible malfunctioning of the device.

A large number of hollow fibers 21 are mounted to extend between end walls 12 and 13, suitably with mounting means such as blocks 22 and 23 adjacent the end walls. The blocks are suitably formed by polymerizing a biologically inert polymer precursor, resin, in situ. Effective polymers for this purpose include castable polyurethane, acrylic or a silicon rubber (e.g., Dow Corning Silastic ® 382 diluted with 360 Medical Fluid for viscosity control). The blocks are formed so as to leave cavities 24 and 26 between walls 12 and 13 and the facing surfaces of blocks 22 and 23, respectively. The area exterior of fibers 21, between blocks 22 and 23, and within the walls of the housing define a medium chamber 30. The aqueous slurry enters through port 15 or 15a and the other port provides an air exit. To assure fluid communication from cavities 24 and 26 into the fibers and optimize membrane surface area prior to mounting walls 12 and 13, the facing surfaces of the blocks are designated and engineered to avoid plugging of openings by the resin.

Fibers 21 are of a conventional type used in the hollow fiber kidney. Suitable ones are made of cellulose or cellulose acetate, or an anisotropic polysulfone membrane developed by Amicon Corp., Lexington, Mass., ranging in size from 180 to 250 microns in internal diameter with wall thickness of about 10 to 30 microns. Other suitable hollow fiber capillaries utilized are Cuprophane ® (Enka Glanzstoff AG). These fibers have an internal diameter of 260 microns and a wall thickness of 20 microns.

When blood is flowing through the device for hemodialysis, it enters port 27 and fills cavity 24, passes through hollow fibers 21 into cavity 26 and its withdrawn through port 28. Blocks 22 and 23 form a tight seal to prevent blood from flowing around the fibers into chamber 30. Except for the shape of the above device conforming to the patient's arm and the components in chamber 30 set forth below, reference may be had to a conventional hollow fiber kidney for the foregoing details of construction and materials.

Figure 4:
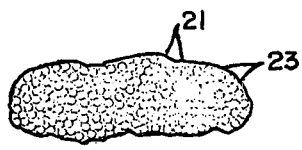
FIG. 4 is an enlarged end view of a portion of FIG. 2.

Referring to FIGS. 4 and 5, fiber separating or spreading means comprises thin parallel plastic sheets or molded ribs 35a extending through blocks 22 and 23 transverse to the fibers to align the fibers in relatively straight channels so that they are exposed to a full 360° to the aqueous slurry medium. Sheets 35 are suitably mounted by adhesion to the inner walls of the housing or can be molded as an integral part of the injection-molded plastic housing.

The most important difference between the conventional fiber kidney device and the present hemodialysis assist device is that in the former, dialysate fluid travels continuously through chamber 30 whereas a stationary nonflowing thixotropic slurry medium is used in the present invention. In an alternative embodiment, blood may flow to the exterior of the fibers and the thixotropic sorbents slurry medium is disposed inside the fiber lumens.

In FIG. 6, a schematic cross-sectional view of a flat plate-type hemodialysis unit is shown in which the thixotropic sorbents slurry medium is highly magnified. The membranes 74 separate the blood flowthrough passage 75 from the nonflowing thixotropic slurry medium chambers 76. Individual sorbent particles are formed into an open three-dimensional thixotropic network slurry structure of interconnecting chain-like or grape-like aggregates 78. In one embodiment, the particles are supplied to chambers 76 in dry powder form and the fluid for the slurry structure is formed from plasma filtrate across the membrane. As described more fully below, such sorbent particles comprise charcoal phosphate ion-binding particles and mixtures of the same.

It is known from polymer or paint coating technology that in an electrolytic solution extremely small particles of carbon black tend to form a slurry network structure with bonds varying from weak physical attraction to chemical bonds between particles. It is also known that when such aggregates form, the slurry becomes thixotropic and the aggregates become highly adherent to surfaces. This contributes to the ability of a wet thixotropic sorbents film to remain stationary on a vertical surface. It has been found that in chamber 76, in the presence of electrolytic fluids, either plasma filtrate or an isotonic solution, the aggregates of sorbent particles physically adhere to the membrane walls forming a highly concentrated but open network at the interface walls in comparison to the region away from the membrane walls. This concentrated porous network yields highly efficient adsorption as the major portion of toxin removal occurs at the membrane interface on the dialysate side.

The size of the sorbent particles is critical to the formation of the thixotropic network. Referring to charcoal, at about 100–150 microns average particle size or less, a substantial open network of aggregates is formed which is significantly more effective in toxin removal than a sorbents slurry of larger particle size as illustrated in the below tables. The particles may be as small as 0.1 micron average size. This increased efficiency is more pronounced than the expected effect of decreasing particle size to increase surface area available for adsorption. Thus, toxin-removal efficiency sharply increases in the vicinity of the critical size limitation.

As discussed above, the sorbents slurry, preferably formed from plasma filtrate, includes fine activated particles forming a viscous thicotropix or gel-like slurry. The thixotropic nature of the slurry causes the sorbent particles to be retained in a relatively fixed position within the sorbent chamber because of the structural integrity of the three-dimensional network. This fixed position is maintained in the presence of a transmembrane positive or negative pressure applied to chamber 30 for the purpose of removing excess body fluids from the blood. The activated charcoal particles serve to adsorb metabolic toxic wastes such as uric acid and creatinine as well as middle molecules, ranging from 400 to 5200 molecular weight.

The dialysate slurry medium becomes osmotically self-regulating in response to osmotic pressures developed by a dialysis patient. For example, in a hypertensive or hypotensive patient, the osmotic forces between the blood and dialysate slurry are rapidly balanced and accomodated. No damage to the dialysis membrane occurs because the swellable sorbents are not chemically bonded to the membranes.

As set out above, because of the thixotropic network matrix of the fine slurry medium, individual sorbent particles cling to one another in chain-like or aggregate formations forming a porous network of high adsorption efficiency. This phenomenon has another extremely important consequence in dialysis. Should a membrane pinhole or tear be present, as is common, then the thixotropic slurry network markedly hinders sorbent particles from being released from the dialysate side and into the blood stream. The chances of leakage through such pinholes or tears is lowered further because the thixotropic dialysate fluid is not being pumped or recirculated in contrast to recirculating dialysate by a pump in conventional dialysis systems. The presence of these chains or aggregates permits the use of very fine sorbent particles with consequently higher surface area and adsorption efficiency but with less chance for leakage through membrane pinholes and tears than the larger unaggregated particles. In summary, the fine sorbent particles of critical size are more efficient adsorbers and safer.

A number of in vitro experiments were performed which establish the criticality of activated charcoal sorbent particle size to removal of middle molecular weight (400–5200 m.w. range), toxins (creatinine, uric acid), and a typical middle molecular weight molecule, Vitamin $B_{12}$. It was determined that these substances were removed far more efficiently when the particles were small enough, i.e., less than 150 microns average particle size, to form a thixotropic network. The results are set out in Table 1. In each instance, the waste blood solution was flowed at 200 ml/min at 37° C. Cuprophane ® membranes (5 microns thick) in a parallel plate dialyzer having 0.8 square meters surface area was used with non-flowing dialysate and a transmembrane pressure of 200 mm Hg.

TABLE 1

Effect of Average Diameter of Powdered Activated Charcoal (Dialysate Side) on Toxin Removal from Blood

| Solute Mean Concentration in mg percent, (mg/100 ml) | Adsorption (hours) | Toxic Removal or Adsorption (mg per gm) |
|---|---|---|
| 0.1–1.0 microns (submicron) | | |
| creatinine | 1 | 195 |
| (10 mg %) | 2 | 228 |
| uric acid | 1 | 260 |
| (8 mg %) | 2 | 380 |
| Vitamin $B_{12}$ | 1 | 75 |
| (12 mg %) | 2 | 84 |
| | 3 | 99 |

TABLE 1-continued

Effect of Average Diameter of Powdered Activated Charcoal (Dialysate Side) on Toxin Removal from Blood

| Solute Mean Concentration in mg percent, (mg/100 ml) | Adsorption (hours) | Toxic Removal or Adsorption (mg per gm) |
|---|---|---|
| 1.0 microns | | |
| creatinine | 1 | 135 |
| (10 mg %) | 2 | 195 |
| uric acid | 1 | 240 |
| (8 mg %) | 2 | 350 |
| Vitamin $B_{12}$ | 1 | 56 |
| (12 mg %) | 2 | 80 |
| | 3 | 95 |
| 12 microns | | |
| creatinine | 1 | 104 |
| (10 mg %) | 2 | 145 |
| uric acid | 1 | 220 |
| (8 mg %) | 2 | 350 |
| Vitamin $B_{12}$ | 1 | 34 |
| (12 mg %) | 2 | 65 |
| | 3 | 85 |
| 75 microns (200 mesh) | | |
| creatinine | 1 | 88 |
| (10 mg %) | 2 | 110 |
| uric acid | 1 | 180 |
| (8 mg %) | 2 | 210 |
| Vitamin $B_{12}$ | 1 | 26 |
| (12 mg %) | 2 | 39 |
| | 3 | 46 |
| 105 microns (150 mesh) | | |
| creatinine | 1 | 65 |
| (10 mg %) | 2 | 89 |
| uric acid | 1 | 135 |
| (8 mg %) | 2 | 160 |
| Vitamin $B_{12}$ | 1 | 18 |
| (12 mg %) | 2 | 25 |
| | 3 | 40 |
| 150 microns (100 mesh) | | |
| creatinine | 1 | 58 |
| (10 mg %) | 2 | 65 |
| uric acid | 1 | 105 |
| (8 mg %) | 2 | 140 |
| Vitamin $B_{12}$ | 1 | 18 |
| (12 mg %) | 2 | 21 |
| | 3 | 29 |
| 200 microns (70 mesh) | | |
| creatinine | 1 | 18 |
| (10 mg %) | 2 | 24 |
| uric acid | 1 | 34 |
| (8 mg %) | 2 | 41 |
| Vitamin $B_{12}$ | 1 | 10 |
| (12 mg %) | 2 | 13 |
| | 3 | 14 |
| 260 microns (50 mesh) | | |
| creatinine | 1 | 21 |
| (10 mg %) | 2 | 37 |
| uric acid | 1 | 33 |
| (8 mg %) | 2 | 57 |
| Vitamin $B_{12}$ | 1 | 6 |
| (12 mg %) | 2 | 7 |
| | 3 | 7 |
| 830 microns (20 mesh) | | |
| creatinine | 1 | 15 |
| (10 mg %) | 2 | 28 |
| uric acid | 1 | 18 |
| (8 mg %) | 2 | 36 |
| Vitamin $B_{12}$ | 1 | 3 |
| (12 mg %) | 2 | 4 |
| | 3 | 5 |

Another advantage of the present device is the effective removal of lipids (triglycerides and cholesterol). This is important because the main cause of death of dialysis patients is heart disease which is directly related to high lipid levels in the patients. Such lipids constitute middle (400–5200) molecular weight toxic substances. The results are set out below in Table 2. (The same test conditions were employed as in Table 1.) No particle release was noted in the experiments.

TABLE 2

Effect of Average Diameter of Powdered Activated Charcoal (Dialysate Side) on Lipid Removal from Blood

| Solute Mean Concentration (mg percent) | Adsorption Time (hours) | Lipid Removal (mg per gm) |
|---|---|---|
| 0.1-1.0 microns (submicron) | | |
| triglyceride | 1 | 198 |
| (200 mg %) | 2 | 225 |
| cholesterol | 1 | 171 |
| (200 mg %) | 2 | 198 |
| 1.0 microns | | |
| triglyceride | 1 | 170 |
| (200 mg %) | 2 | 185 |
| cholesterol | 1 | 150 |
| (200 mg %) | 2 | 165 |
| 12 microns | | |
| triglyceride | 1 | 145 |
| (200 mg %) | 2 | 138 |
| cholesterol | 1 | 130 |
| (200 mg %) | 2 | 145 |
| 75 microns (200 mesh) | | |
| triglyceride | 1 | 118 |
| (200 mg %) | 2 | 135 |
| cholesterol | 1 | 115 |
| (200 mg %) | 2 | 125 |
| 105 microns (150 mesh) | | |
| triglyceride | 1 | 100 |
| (200 mg %) | 2 | 110 |
| cholesterol | 1 | 95 |
| (200 mg %) | 2 | 115 |
| 150 microns (100 mesh) | | |
| triglyceride | 1 | 95 |
| (200 mg %) | 2 | 150 |
| cholesterol | 1 | 85 |
| (200 mg %) | 2 | 89 |
| 200 microns (70 mesh) | | |
| triglyceride | 1 | 30 |
| (200 mg %) | 2 | 38 |
| cholesterol | 1 | 20 |
| (200 mg %) | 2 | 25 |
| 260 microns (50 mesh) | | |
| triglyceride | 1 | 18 |
| (200 mg %) | 2 | 20 |
| cholesterol | 1 | 11 |
| (200 mg %) | 2 | 12 |
| 830 microns (8 mesh) | | |
| triglyceride | 1 | 8 |
| (200 mg %) | 2 | 10 |
| cholesterol | 1 | 6 |
| (200 mg %) | 2 | 6 |

As set out above, fine commercial phosphate ion-binding particles preferably are included as sorbents to treat the hyperphosphatemia problem in artificial kidney patients. Suitable commercial phosphate ion-binders include anion exchange resin, such as Amberlite IRA-400 (20–50 mesh particle size) sterilized by gas or irradiation, sold by Rohm & Haas Co., Duolite A101-D (20–50 mesh particle size) sold by Diamond Shamrock, and an inorganic ion exchanger, such as aluminum based phosphate-binder, such as aluminum hydroxide, magnesium-based phosphate binder or hydrated zirconium hydroxide. Such binder in the same size range as the charcoal particles forms part of the thixotropic slurry network.

The same relationship between efficiency of removal of middle molecular toxins applies to the size of phosphate binder particles and efficiency of inorganic phosphate removal. This is illustrated below in Table 3 using the conditions of Table 1.

TABLE 3

Effect of Average Diameter of Powdered Aluminum Oxide (Dialysate Side) on Phosphate Removal from Blood

| Solute Mean Concentration (mg percent) | Adsorption Time (hours) | Phosphate Removal (mg/gm) |
|---|---|---|
| *0.1–1.0 microns (submicron)* | | |
| inorganic phosphate (10 mg %) | 1 | 65 |
| | 2 | 89 |
| *1 micron* | | |
| inorganic phosphate (10 mg %) | 1 | 46 |
| | 2 | 66 |
| *50 microns* | | |
| inorganic phosphate (10 mg %) | 1 | 38 |
| | 2 | 45 |
| *110 microns* | | |
| inorganic phosphate (10 mg %) | 1 | 36 |
| | 2 | 39 |
| *150 microns (100 mesh)* | | |
| inorganic phosphate (10 mg %) | 1 | 31 |
| | 2 | 36 |
| *200 microns (70 mesh)* | | |
| inorganic phosphate (10 mg %) | 1 | 13 |
| | 2 | 16 |
| *260 microns (50 mesh)* | | |
| inorganic phosphate (10 mg %) | 1 | 11 |
| | 2 | 14 |
| *830 microns (20 mesh)* | | |
| inorganic phosphate (10 mg %) | 1 | 4 |
| | 2 | 5 |

The solids content (charcoal powder and phosphate ion-binding particles) required for the assist device is dependent upon a number of facts including the condition of the patient, the efficiency of the conventional hemodialyzer unit and the available transfer area of the membrane in the assist unit. In a typical unit, the total solids content should be as high as practical to form a dispersed thixotropic aqueous slurry, say, as high as 25–75% or 40–60% by weight. An advantage of such a thixotropic slurry is that a high percentage of sorbent particles per unit volume may be packed. A total solids content may be on the order of 125–250 grams per hemodialysis assist device. Since high efficiency phosphate removal assists reduction of treatment time, it may constitute a high proportion of total solids content, say 50–70% by weight, with the balance of activated carbon powder.

The data in Tables 1–3 show that the thixotropic sorbent slurry together with thin dialysis membranes provide a marked increase in kinetic performance. It is believed that this is caused by toxin diffusion over relatively smaller distances due to the excellent bonding of sorbents at the membrane interface.

In one convenient technique for packing the sorbent dialysate chamber, the sorbent (activated carbon powder alone or with phosphate binding powder) is placed in dry form in the sorbent medium chamber, after the unit has been conventionally manufactured and assembled. The filled unit is then sterilized and shipped for use. The thixotropic network is formed in situ by plasma during ultrafiltration or by the addition of standard saline solution.

In a preferred embodiment, the sorbent medium includes a blood compatible hydrophilic cellulose-base polymer fine powder capable of forming a thixotropic network of the same general character as that set forth with respect to the sorbent particles. The average particle size is less than 3 microns and typically 1–3 microns or less. These particles form interlinking chain-like aggregates which interlock into the open thixotropic network slurry structure of sorbent particles.

This cellulose-base polymer binder may be of a number of known cellulose or modified-cellulose types. Suitable forms include microcrystalline cellulose, alkyl-substituted cellulose, and regenerated cellulose. Specific alkyl substituted cellulose particles include methylcellulose, ethylcellulose, hydroxypropylcellulose, and carboxymethylcellulose.

A preferred form of binder is a microcrystalline cellulose. Suitable products of this type are sold under the trademark Avicel and Avirin by FMC Corporation. Typically, the microcrystalline aggregates range in diameter from 150–300 angstroms to about 5 microns. Gels formed from these products are thixotropic and provide an extremely stable vehicle for suspending particulate matter, such as the foregoing sorbent particles. Suitable concentrations of such binder are from about 0.5 weight % to 6 weight % based on the sorbent particles solids content.

The foregoing polymer binder serves as both a thickening agent and film former. Its presence provides a controlled viscosity and adhesivity to the mixture to facilitate manufacture of a device. For example, a slurry of the sorbent particles and polymer binder may be coated onto the semi-permeable membrane. Thus, for example, when forming a device of the hollow fiber type, bundles of the fibers formed of membranes may be contacted with a volume of slurry as by dipping to coat a layer of say 10–16 microns in thickness onto the exterior of the fibers. The polymer binder facilitates such coating. Thereafter, the fibers may be dried leaving a coating on the hollow fibers. If desired, this procedure may be repeated again contacting the fibers with the sorbent slurry bath to provide a thicker coating of up to 30–40 microns if desired. Then, the coating on the fibers may be dried to provide a set coated layer which is highly porous and serves as a resilient mechanical support for the membrane.

The foregoing coated fibers may be then assembled into a device of the hollow fiber type and shipped for use. A thixotropic network may be formed in situ by plasma during ultrafiltration or by addition of standard saline solution as set out above.

Another important function of the polymer binder is its assistance in retaining the sorbents in place during ultrafiltration at high transmembrane pressures. The presence of a small amount of such polymer binder together with the charcoal powder increases the overall viscosity of the mixture, provides a stable gel suspension, reinforces the adhesion of the aggregate chains to the membrane, and generally provides resistance to mechanical shock or vibration.

In the sorbents thixotropic medium alone or, in combination with the present polymer binder also serves to provide mechanical support to the dialysis membrane. The use of this thixotropic slurry support permits the use of membranes of less than 10 microns in thickness, typically 5–8 microns, in comparison to conventional membranes on the order of 10–15 microns. One advantage of using such thin membranes is the increased efficiency of removing urea during ultrafiltration. For example, urea is removed at a clearance rate of 150 ml/min. square meter using a Cuprophane ® dialysis membrane of 5 microns thickness. This is a 20 to 25% improvement over normal clearance rates for urea using Cuprophane ® dialysis membranes thicker than 10 to 15 microns.

Another advantage of such thin membranes is that a maximum amount of middle molecules are removed during ultrafiltration, for example, 60 ml/min square meter of vitamin $B_{12}$. This is a 100-150% improvement in clearing vitamin $B_{12}$ over the normal clearance rate for thicker dialysis membrane dialyzers.

It has been found that a relatively minor amount of thixotropic polymer binder provides the above varied beneficial effects in the present sorbent system. Thus, 0.5% to 6% and preferably 1 to 3% by weight of binder based upon dry solids content are sufficient for purposes of the present invention. It is preferable that this polymer binder comprise essentially the entire amount of total polymer in the sorbent in contrast to the aforementioned Grossman device which includes many times this amount of polymer.

It has been found that the foregoing polymer binder does not substantially mask the effectiveness of the sorbents for performing their function. By way of example, Table 4 illustrates the effective average diameter of powdered activiated charcoal dispersed in thixotropic cellulose of the Avicel type at a ratio of 3% polymer and 97% charcoal.

It is apparent that the results are comparable to those set out in Table 1 which does not include the polymer binder.

TABLE 4

Effect of Average Diameter of Powdered Activated Charcoal Dispersed in Thixotropic Cellulose (submicron average particle size) Binder (Dialysate Side) on Toxin Removal from Blood

| Solute Mean Concentration in mg %, (mg/100 ml) | Adsorption (hours) | Toxic Removal of Adsorption (mg per gm) |
|---|---|---|
| 0.1–1.0 microns (submicron) | | |
| creatinine | 1 | 125 |
| (10 mg %) | 2 | 180 |
| uric acid | 1 | 145 |
| (8 mg %) | 2 | 205 |
| Vitamin $B_{12}$ | 1 | 70 |
| (12 mg %) | 2 | 75 |
| 12 microns | | |
| creatinine | 1 | 94 |
| (10 mg %) | 2 | 100 |
| uric acid | 1 | 135 |
| (8 mg %) | 2 | 170 |
| Vitamin $B_{12}$ | 1 | 35 |
| (12 mg %) | 2 | 45 |
| 75 microns (200 mesh) | | |
| creatinine | 1 | 72 |
| (10 mg %) | 2 | 81 |
| uric acid | 1 | 170 |
| (12 mg %) | 2 | 200 |
| Vitamin $B_{12}$ | 1 | 38 |
| (8 mg %) | 2 | 45 |
| 150 microns (100 mesh) | | |
| creatinine | 1 | 59 |
| (10 mg %) | 2 | 70 |
| uric acid | 1 | 100 |
| (12 mg %) | 2 | 120 |
| Vitamin $B_{12}$ | 1 | 18 |
| (8 mg %) | 2 | 20 |
| 260 microns (50 mesh) | | |
| creatinine | 1 | 20 |
| (10 mg %) | 2 | 34 |
| uric acid | 1 | 28 |
| (8 mg %) | 2 | 50 |
| Vitamin $B_{12}$ | 1 | 5 |
| (12 mg %) | 2 | 6 |
| 830 microns (20 mesh) | | |
| creatinine | 1 | 11 |
| (10 mg %) | 2 | 17 |
| uric acid | 1 | 15 |
| (8 mg %) | 2 | 25 |

TABLE 4-continued

Effect of Average Diameter of Powdered Activated Charcoal Dispersed in Thixotropic Cellulose (submicron average particle size) Binder (Dialysate Side) on Toxin Removal from Blood

| Solute Mean Concentration in mg %, (mg/100 ml) | Adsorption (hours) | Toxic Removal of Adsorption (mg per gm) |
|---|---|---|
| Vitamin $B_{12}$ | 1 | 3 |
| (12 mg %) | 2 | 3 |

Referring to FIG. 1, a contour-shaped hemodialysis assist housing of the foregoing type is illustrated as being worn on the upper arm of the patient between the elbow and wrist suitably appended by elastic arm band 36. The housing also includes ports 37 and 37a for the initial supply of the aqueous slurry network and also for ultrafiltration of water from the blood. Ports 37 and 38a suitably include plus 38 and 38a. Plug 38 is retained in place except during ultrafiltration. In the illustrated embodiment, blood is removed from an artery of the patient's arm via arterial tubing 40 through a conventional connection (not shown). After passing through the assist device, the blood is passed through tubing 42 to a conventional hemodialyzer with flowing dialysate fluid. Then, the blood is returned to the patient's blood system into the patient's vein through a venous tubing and conventional connection (not shown). Blood access may be made by a conventional fistula route. Alternatively, it may be performed by a Scribner A-V shunt. The single needle fistula type may be employed. However, this fistula technique requires a positive displacement micropump to provide an adequate blood flow rate.

Any conventional hemodialyzer can be used in combination with the assist device. Suitable ones include the flat membrane hemodialyzer, or a hollow-fiber type (Cordis-Dow), or a parallel-flow hemodialyzer (Travenol Co.) or the Vivacell hemicapillary hemodialyzer (B.D. Life Support Systems). The dialysate compartments of any of these conventional hemodialyzers can be filled with the sorbents mixture and thus be converted to a hemodialysis assist device.

In arterial tubing 40, a heparin-injection sleeve 44 may be provided for the supply of heparin to prevent blood coagulation within the device. Two filters 46a and 46b of a conventional filter type containing dacron fibers is provided for the removal of possible particulate material, such as debris and microemboli in the patient's blood. It has been found that only one blood microfilter (using medium or fine grade dacron fibers) inserted between the venous sensor cube and the venous side of the shunt or fistula is adequate for this purpose. Two additional arterial microfilers containing coarse-grade dacron fiber is an extra safety filter, but is not essential.

Means is provided for detecting abnormal blood pressure or blood temperature readings which indicate a possible malfunction of the device. Such means includes an arterial sensor cube 47 and a venous sensor cube 48 connected by means of sensor cable 49 to intrumentation package 50. This package, suitably battery charged and capable of being worn on the patient's belt or the like, includes visual indicators, lights 51 and an audio indicator, speaker 52, connected to suitable electronics for actuation upon malfunctioning of the foregoing type. The above monitoring controls are normally included with conventional hemodialyzers and so may be eliminated.

Typical operation of the foregoing device is as follows. The assist device is connected in series with a conventional flowing dialysate artificial kidney device. Treatment time is substantially reduced (by as much as 25% to 50%) without hyperphosphatemic and fluids-retention problems. Auxiliary ultrafiltration may be performed during dialysis. The excess body fluids can be collected either by a plastic drain bag or a collection flask.

A typical hollow fiber type artificial kidney is characterized as follows. The housing is formed of transparent polycarbonate or acrylate plastic material molded to fit the arm, leg, or abdomen contour or of a typical dimension: width—11.0 cm; depth—2.6 cm; and length—16 cm; typical filled weight—585 gm; and blood priming volume—50 ml. The hollow fibers are characterized by: number—12,000; effective length—12 cm; inside diameter—200 microns; and wall thickness—10 to 12 microns.

Conventional sterilization techniques to kill microbacteria and germs may be used for the foregoing device after which the device can be sealed and stored in a cool place. The dry sorbent powders may be initially sterilized by dry thermal treatment and then placed in the dialysate compartment. The device may then be conventionally sterilized as by gamma-irradiation for 2 to 3 hours.

In another embodiment of the invention, a plate type artificial kidney device may be employed using any parallel-flow membrane structure conventionally employed with flowing dialysate fluids. As set forth above, the improvement of the invention is the substitution of the foregoing thixotropic sorbents slurry for the flowing dialysate fluid. A suitable structure is supplied under the trademark "The Gambro Lundia Nova Dialyzer". This package includes a disposable 17 layer parallel flow design. The membrane employed in the dialyzer is Cuprophane ®. Since a viscous slurry sorbent replaces the flowing dialysate fluid conventional system, two access tapered openings are employed on the dialysate side of the plates; one for the sorbents slurry and the other as an exit for air during injection.

Referring specifically to FIG. 3, a schematic view of a plastic plate type internal configuration is illustrated with the depth dimension transverse to the direction of flow exaggerated for clarity. Also, only six flowthrough passages are illustrated since they are identical. The device includes plates 61 and 62 surrounding an elongated Cuprophane ® semipermeable membrane 63 defining a flowthrough passage. Membrane 63 has an elliptical cross-section when expanded by blood flowing through the same extending along the width of housing 60 in blood flowthrough passage 65. One surface of plate 62 faces an adjacent surface of membrane 63 while the other surface of plate 62 faces an adjacent membrane, not shown, on the opposite side. In this manner, the entire device is stacked with the desired number of blood flowthrough passages. The area between the opposed surfaces of plates 61 and 62 and the corresponding surface of membrane 63 defines a chamber 64 in which the aqueous slurry medium 66 of the present invention is disposed sealed from contact with passage 65. Blood cavities 67 and 68 are in communication with blood inlet port 69 and outlet port 70, respectively, and also with blood flowthrough passage 65.

A manifold 72 is provided with connecting tubing 73 communicating with the interior of chamber 66 for supplying the slurry to chamber 64. An outlet manifold 71 is provided for removing air during filling of aqueous sorbents slurry.

Figure 2:
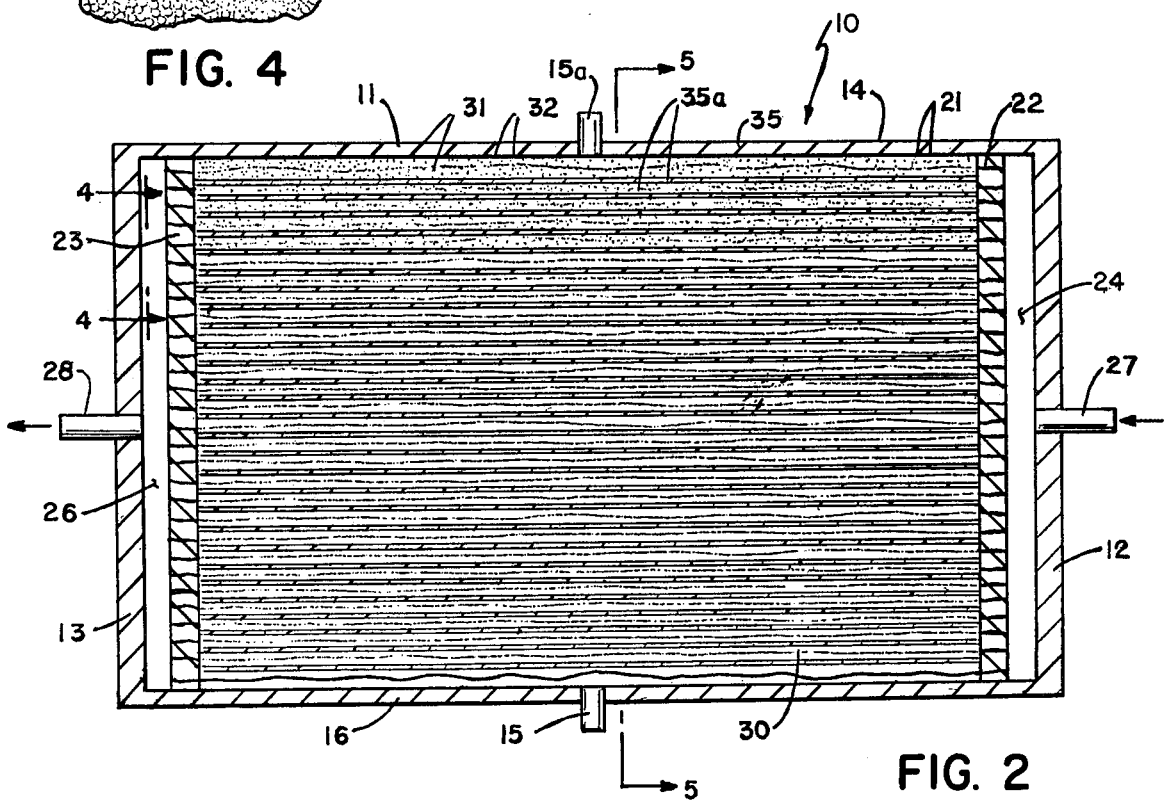

The principle of operation of the device of FIG. 2 is the same as the one set forth above with respect to the hollow fiber artificial kidney device. Blood is supplied to port 69 via arterial tubing and is passed through a conventional hemodialyzer and returned to the patient's blood stream via venous tubing connecting at port 70.

It is apparent that an effective hemodialysis assist device has been provided which is effective to reduce the time of hemodialysis, to actively remove urea, and to reduce the dangers of hyperphosphatemia, hyperlipidemia, and fluids-retention. Although the foregoing description illustrates the hollow capillary and parallel-flow membrane types of internal configuration, it is apparent that any other dialysate configuration may be employed so long as the blood flows through a blood flowthrough passage bounded by a semipermeable membrane and a thixotropic slurry medium of the foregoing type is employed adjacent the same. For example, the internal configuration may include pleated flat membranes formed from Cuprophane ® sheets. A hemodialyzer of this type is manufactured under the designation Para-Flow 1600 by Travenol Laboratories of Deerfield, Illinois. Of course, the flowing dialysate fluid of the Travenol device is replaced by the sorbents slurry mixture of the present invention.

What is claimed is:

1. A hemodialysis assist device for removing selected components including urea in a patient's blood stream, said device comprising fluid containing means and at least one blood flowthrough passage separated therefrom by a semipermeable membrane, blood inlet and outlet openings communicating with said blood flowthrough passage, an ultrafiltration port for said fluid containing means, a normally non-flowing fluid blood compatible sorbents medium disposed in said fluid containing means including fine sorbent particles selected from the group consisting of charcoal powder capable of sorbing metabolic toxic wastes, phosphate ion-binding particles and mixtures thereof, said sorbent particles having an average diameter of less than 150 microns and forming an open thixotropic network slurry structure of interconnecting chain-like aggregates of sorbent particles, a portion of said chain-like aggregates being adhered to the fluid containing means side of said membrane forming a concentrated network of sorbent particles on the membrane surface, said sorbents medium including microcrystalline cellulose flour-based binder of an average particle size less than 3 microns and characterized by thixotropic behavior, said cellulose flour based binder forming interlinking chain-like aggregates in the fluid sorbents medium interlocked in the open thixotropic network slurry structure of sorbent particles and serving to assist the adherence of sorbent particles to said membrane to thereby retard loss of sorbent particles at high ultrafiltration flow rates, said thixotropic network being of sufficient structural integrity to be retained substantially in place during ultrafiltration of excess body fluids from the blood through said ultrafiltration port.

2. The device of claim 1 in which said phosphate ion-binding particles are comprised of aluminum hydroxide-based particles.

3. The device of claim 1 in which said sorbent particles comprise said charcoal powder.

4. The device of claim 1 in which said sorbent particles comprise said phosphate ion-binding particles.

5. The device of claim 1 in which the total polymer content of said sorbents slurry consists essentially of said microcrystalline cellulose flour-based binder.

6. The device of claim 1 connected in series with a standard hemodialyzer with flowing dialysate fluid, the blood outlet opening of said hemodialysis assist device being connected by tubing to the inlet side of said standard hemodialyzer.

7. The device of claim 1 in which said cellulose flour-based binder comprises about 0.5 to 6 weight percent based on the sorbents particles solids content.

8. In a method for removing selected components including urea of a patient's blood using a hemodialysis assist device enclosing at least one blood flowthrough passage and at least one semipermeable membrane separating the passage from a fluid containing chamber which contains a normally non-flowing sorbents medium or fine sorbent particles selected from the group consisting of charcoal powder capable of sorbing metabolic toxic wastes and phosphate ion-binding particles and mixtures thereof, said sorbent particles having an average diameter of less than 150 microns and forming an open thixotropic network slurry structure of interconnecting chain-like aggregates of sorbent particles, a portion of said chain-like aggregates being adhered to the fluid containing means side of said membrane forming a concentrated network of sorbent particles on the membrane surface, said sorbents medium including microcrystalline cellulose flour-based binder of a thixotropic character of an average particle size less than 3 microns, said cellulose-based binder forming chain-like aggregates in the fluid sorbents medium interlocked in the open thixotropic network slurry structure of sorbent particles and serving to assist the adherence of sorbent particles to said membrane to thereby retard loss of sorbent particles at high ultrafiltration flow rates, said thixotropic network being of sufficient structural integrity to be retained substantially in place during ultrafiltration of excess body fluids from the blood through the same, the steps of continuously directing blood from a patient through said blood flowthrough passage, and diffusing toxic substances from the blood across the membrane through the aqueous thixotropic network sorbents slurry to bind said sorbents.

9. The method of claim 8 together with the step of ultrafiltrating excess body fluids from the blood through said aqueous slurry thixotropic slurry.

10. The method of claim 8 in which said sorbent particles include said phosphate ion-binding particles, and including the step of diffusing phosphate ions from the blood across the membrane through the aqueous sorbent slurry and to bind to said phosphate ion-binding particles.

11. The method of claim 8 in which the patient's blood is flowed from the outlet side of said device to the inlet side of a standard hemodialyzer which employs flowing dialysate fluid.

12. The method of claim 8 in which said toxic substance is a lipid.

13. The method of claim 8 in which said cellulose flour-based binder comprises about 0.5 to 6 weight percent based on the sorbents particles solids content.

* * * * *